(12) United States Patent
Choi

(10) Patent No.: US 12,714,856 B2
(45) Date of Patent: Aug. 25, 2026

(54) IMPLANTABLE ELECTRICAL STIMULATION (IES) SYSTEM AND A METHOD THEREOF

(71) Applicant: Charles Tak Ming Choi, Hsinchu (TW)

(72) Inventor: Charles Tak Ming Choi, Hsinchu (TW)

( * ) Notice: Subject to any disclaimer, the term of this patent is extended or adjusted under 35 U.S.C. 154(b) by 460 days.

(21) Appl. No.: 18/198,294

(22) Filed: May 17, 2023

(65) Prior Publication Data

US 2024/0009455 A1 Jan. 11, 2024

Related U.S. Application Data

(60) Provisional application No. 63/388,033, filed on Jul. 11, 2022.

(51) Int. Cl.
*A61N 1/36* (2006.01)
*A61N 1/05* (2006.01)

(52) U.S. Cl.
CPC ........ *A61N 1/36039* (2017.08); *A61N 1/0541* (2013.01)

(58) Field of Classification Search
CPC ............ A61N 1/36039; A61N 1/36139; A61N 1/36185; A61N 1/36038; A61N 1/0541
See application file for complete search history.

(56) References Cited

U.S. PATENT DOCUMENTS 6,415,185 B1 7/2002 Maltan
2019/0262609 A1 8/2019 Brill et al.
2020/0330763 A1* 10/2020 Hamacher .......... A61N 1/36038
2021/0178160 A1* 6/2021 Penninger ............ A61N 1/0541
2022/0285005 A1* 9/2022 Noble ................. A61B 5/0536

FOREIGN PATENT DOCUMENTS

CN 112469462 A 3/2021

OTHER PUBLICATIONS

International Search Report of PCT Patent Application No. PCT/CN2023/094810 issued on Sep. 14, 2023.

(Continued)

*Primary Examiner* — Joseph M Dietrich

(57) ABSTRACT

An implantable electrical stimulation (IES) system and a method thereof, is disclosed. The implantable electrical stimulation (IES) system may comprise an implantable electrode array having a plurality of electrode contacts, an electrical stimulus means, a sensor and a processing circuitry. The electrical stimulus means may be configured for applying the electrical stimulus to at least one stimulating electrode contact of the implantable electrode array. The sensor may be configured for sensing and determining a measured ECAP of the at least one stimulating electrode to generate data for determining a plurality of parameters for the at least one stimulating electrode of the implantable electrode array. The processing circuitry may be configured for processing the measured ECAP and plurality of parameters of the at least one stimulating electrode of the implantable electrode array to compute the corresponding parameters for the remaining electrode contacts of the implantable electrode array.

23 Claims, 14 Drawing Sheets

(56) References Cited

OTHER PUBLICATIONS

Tim Brochier et al., Evaluating and Comparing Behavioural and Electrophysiological Estimates of Neural Health in Cochlear Implant Users, Journal of the Association for Research in Otolaryngology, Nov. 4, 2020, pp. 67-80.
Charlotte Garcia et al., SpeedCAP: An Efficient Method for Estimating Neural Activation Patterns Using Electrically Evoked Compound Action-Potentials in Cochlear Implant Users, Ear & Hearing, Dec. 8, 2022, pp. 627-640, vol. 44, No. 3.
Ramos-De-Miguel Ángel et al., A phenomenological computational model of the evoked action potential fitted to human cochlear implant responses, PLOS Computational Biology, May 27, 2022, pp. 1-27, vol. 18, No. 5.
Charlotte Garcia et al., The Panoramic ECAP Method: Estimating Patient-Specific Patterns of Current Spread and Neural Health in Cochlear Implant Users, Journal of the Association for Research in Otolaryngology, Apr. 23, 2021, pp. 567-589.

* cited by examiner

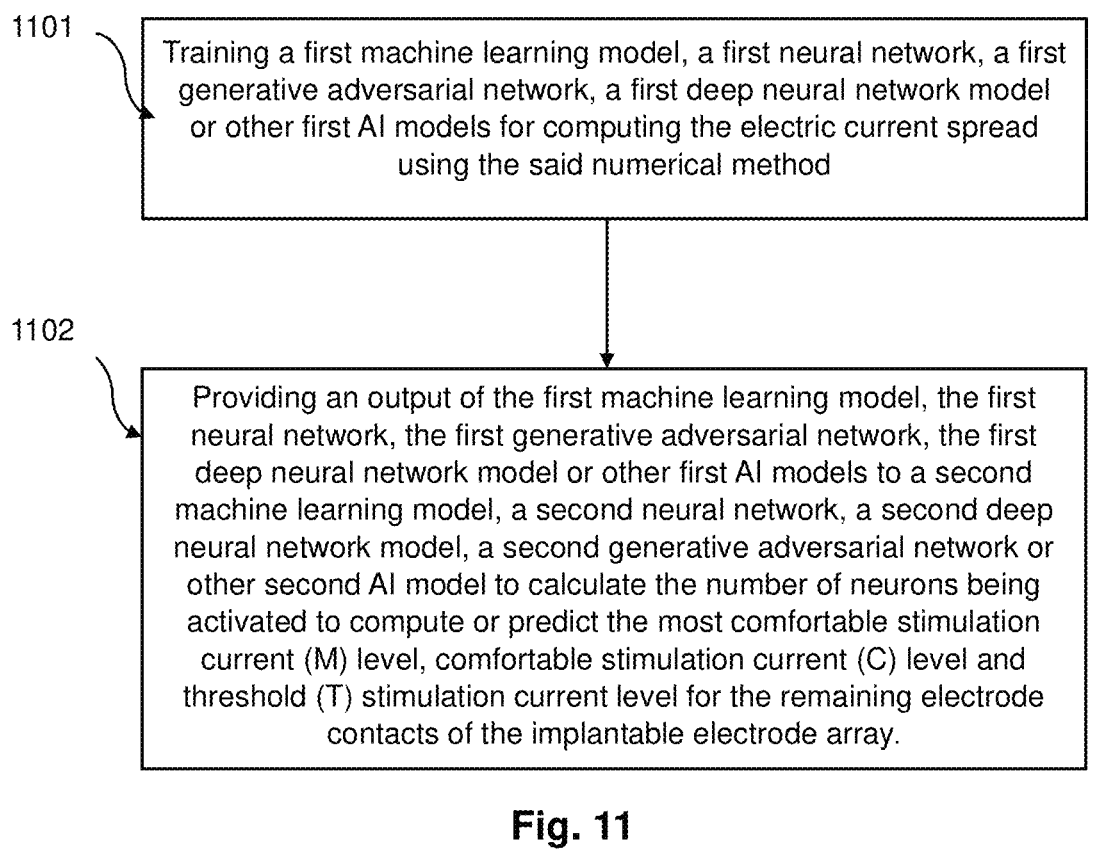

1101

Training a first machine learning model, a first neural network, a first generative adversarial network, a first deep neural network model or other first AI models for computing the electric current spread using the said numerical method

1102

Providing an output of the first machine learning model, the first neural network, the first generative adversarial network, the first deep neural network model or other first AI models to a second machine learning model, a second neural network, a second deep neural network model, a second generative adversarial network or other second AI model to calculate the number of neurons being activated to compute or predict the most comfortable stimulation current (M) level, comfortable stimulation current (C) level and threshold (T) stimulation current level for the remaining electrode contacts of the implantable electrode array.

Fig. 11

IMPLANTABLE ELECTRICAL STIMULATION (IES) SYSTEM AND A METHOD THEREOF

CROSS-REFERENCE TO RELATED APPLICATIONS AND PRIORITY

The present application claims priority from U.S. Provisional Patent Application No. 63/388,033 filed on Jul. 11, 2022, the entirety of which is incorporated herein by a reference.

TECHNICAL FIELD

The present application described herein, in general, relates to an implantable electrical stimulation (IES) system and a method thereof. More particularly, the present application related to an implantable electrical stimulation (IES) system, including, but not limited to, cochlear implants stimulation, spinal cord stimulation, retinal prosthesis stimulation, vagal nerve stimulation, deep brain stimulation, kidney implant stimulation, gastric electrical stimulation for gastroparesis, intestinal electrical stimulation, electrical stimulation for urinary incontinence, intravaginal electrical stimulation, electrical muscular stimulation, transcranial electrical stimulation, occipital nerve stimulation, brain cortical stimulation and other electrical stimulations.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Cochlear implant (CI) users are required to visit cochlear implant centers post-operatively to be programmed for the first visit (the turn-on) and reprogrammed at regularly scheduled intervals to reprogram their cochlear implants throughout their lifetime. Typically, the maximum and minimum current levels (corresponding to the M or C and the T levels clinically) for each CI electrode have to be found by subjective feedback. Here 'M' refers to "Most Comfortable Stimulation Current", 'C' refers to "Comfortable Stimulation Current" and 'T' refers to "Threshold (T) Stimulation Current". Sometimes, an objective method like electrically evoked compound action potential (ECAP) is used to supplement the subjective response, particularly in the pediatric cases. Unfortunately, ECAP threshold levels' correlation with M or C and T levels can vary and be inconsistent in the performance. Further, there is no easy and obvious way to know which CI users can utilize their ECAP thresholds for CI programming. Typically, it is difficult to program pediatric CI users due to their inability to communicate precisely and their lack of language skills due to their severe to profound hearing impairment. The M or C, and T levels constitute a MAP for a CI user.

Typically, the cochlear implant (CI) clinical audiologists may choose four electrodes (choose one electrode in electrodes 1-4, 5-8, 9-12 and 13-16 for the 16-electrode systems, similarly for 22-electrode systems) to be programmed or mapped. The well-established standard of CI programming or mapping is to measure the M/C/T levels using behavior measurements. Typically, it takes at least 20 to 30 minutes if not less to measure the M/C/T levels per electrode using behavior measurements. Typically, up to 4 electrodes can be mapped or programmed within a two-hour mapping session, then the M/C/T levels can be used to extrapolate to the rest of the 12 electrodes for a 16-electrode CI system. Although the mapping of adult CI users may be straightforward and relatively easy, it is difficult to map 1 to 6-year-old CI users since they have no concept of communication. 1 to 6-year-old CI users are implanted with CI due to the fact that they have no hearing. Further, it is difficult to ask a 1 to 6-year-old CI user to sit still to be mapped or programmed for 1.5-2 hours. Therefore, the conventional behavior measurement method takes a lot of time to program or map all 4 electrodes in a 1 to 6-year-old CI user. Therefore, there is a long-standing clinical need to reduce the overall behavior measurement time.

Further, an electric field imaging (EFI) measurement is used in clinical CI mapping sessions to check whether the CI system/model is working normally. However, EFI measurement is not used in improving the accuracy of CI systems/models.

One of such Cochlear implant (CI) is proposed in U.S. Pat. No. 6,415,185 Bi which discloses a method of objectively gathering stimulation data associated with programming an implantable cochlea stimulation (ICS) system. A myogenic-based evoked response (MER) is deliberately sensed and measured with permanently implanted electrodes connected to a Cochlear implant device. The measured MER is then used to assist in the objective programming of the Cochlear implant. The MER may be measured between two intra-Cochlear electrodes, between one intra-Cochlear electrode and one extra-Cochlear reference electrode, or between two extra-Cochlear electrodes. Since the measured MER is believed to pre-empt the actual stapedius reflex, the electrodes need not be placed into or in close proximity to the stapedial tendon, the stapes, or the facial nerve.

Further, a technique such as forward-masked electrically evoked compound action potentials (ECAPs) to estimate neural activation patterns of CI stimulation is disclosed in the "Panoramic ECAP Method: Estimating Patient-Specific Patterns of Current Spread and Neural Health in Cochlear Implant Users, Journal of the Association for Research in Otolaryngology, pp. 567-589, 2021 DOI: 10.1007/s10162-021-00795-2." However, the disclosed technique only focuses on producing detailed estimates of neural activation patterns by modeling current spread and neural health.

Furthermore, a published paper "a phenomenological computational model of the evoked action potential fitted to human cochlear implant responses" PLoS Comput Biol 18(5): e1010134. https://doi.org/10.1371/journal.pcbi.1010134 discloses about study of ECAP based on the finite element model and neuron model. However, the published paper only focuses on modeling ECAPs.

Therefore, there is a long-standing need for an improved system and a method for an implantable electrical stimulation (IES) which can alleviate at least the drawbacks and/or challenges associated with the conventional IES systems.

SUMMARY

This summary is provided to introduce concepts related to an implantable electrical stimulation (IES) system, an apparatus, a non-transitory computer readable medium, and a method thereof and the concepts are further described below in the detailed description. This summary is not intended to identify essential features of the claimed subject matter nor it is intended for use in determining or limiting the scope of the claimed subject matter.

In one implementation, an implantable electrical stimulation (IES) system is disclosed. The implantable electrical stimulation (IES) system may include an implantable electrode array having a plurality of electrode contacts, an electrical stimulus means, a sensor and a processing circuitry. The electrical stimulus means may be configured for applying the electrical stimulus to at least one stimulating electrode contact of the implantable electrode array. The sensor may be configured for sensing and determining a measured evoked compound action potential (ECAP) of the at least one stimulating electrode contact to generate data for determining a plurality of parameters for the at least one stimulating electrode contact of the implantable electrode array. The processing circuitry may be configured for processing the measured ECAP and the plurality of parameters of the at least one stimulating electrode contact of the implantable electrode array to compute the corresponding parameters for the remaining electrode contacts of the implantable electrode array.

In another implementation, a method for an implantable electrical stimulation (IES) is disclosed. The method may include providing an implantable electrode array having a plurality of electrode contacts. The method may further include applying, via an electrical stimulus means, the electrical stimulus to at least one stimulating electrode contact of the implantable electrode array. The method may further include sensing and determining, via a sensor, a measured evoked compound action potential (ECAP) of the at least one stimulating electrode contact to generate data for determining a plurality of parameters for the at least one stimulating electrode contact the implantable electrode array. Furthermore, the method may include processing, via a processing circuitry, the measured ECAP and the plurality of parameters for computing the corresponding parameters for the remaining electrodes of the implantable electrode array.

In yet another implementation, an apparatus enabling an implantable electrical stimulation (IES) is disclosed. The apparatus may include an implantable electrode array having a plurality of electrode contacts, an electrical stimulus means, a sensor and a processing circuitry. The electrical stimulus means may be configured for applying the electrical stimulus to at least one stimulating electrode contact of the implantable electrode array. The sensor may be configured for sensing and determining a measured evoked compound action potential (ECAP) of the at least one stimulating electrode contact to generate data for determining a plurality of parameters for the at least one stimulating electrode contact of the implantable electrode array. The processing circuitry may be configured for processing the measured ECAP and the plurality of parameters of the at least one stimulating electrode contact of the implantable electrode array to compute the corresponding parameters for the remaining electrode contacts of the implantable electrode array.

In still another implementation, a non-transitory computer readable medium storing a program for enabling implantable electrical stimulation (IES), is disclosed. The program may include a plurality of programmed instructions executed by a processing circuitry. The plurality of programmed instructions may include instructions for receiving a measured evoked compound action potential (ECAP) of the at least one stimulating electrode contact of an implantable electrode array from a sensor to generate data for determining a plurality of parameters for the at least one stimulating electrode contact of the implantable electrode array. Further, the plurality of programmed instructions may include instructions for processing the measured ECAP and the plurality of parameters of the at least one stimulating electrode contact of the implantable electrode array to compute the corresponding parameters for the remaining electrode contacts of the implantable electrode array.

BRIEF DESCRIPTION OF THE DRAWINGS

The detailed description is described with reference to the accompanying figures. Some embodiments of device and method in accordance with embodiments of the present subject matter are now described, by way of example only, and with reference to the accompanying figures.

FIG. 11 illustrates a fifth method of an artificial intelligence (AI) based method for the implantable stimulation implant (IES), in accordance with a fifth embodiment of the present application.

DETAILED DESCRIPTION

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures or characteristics may be combined in any suitable manner in one or more embodiments.

Figure 1:
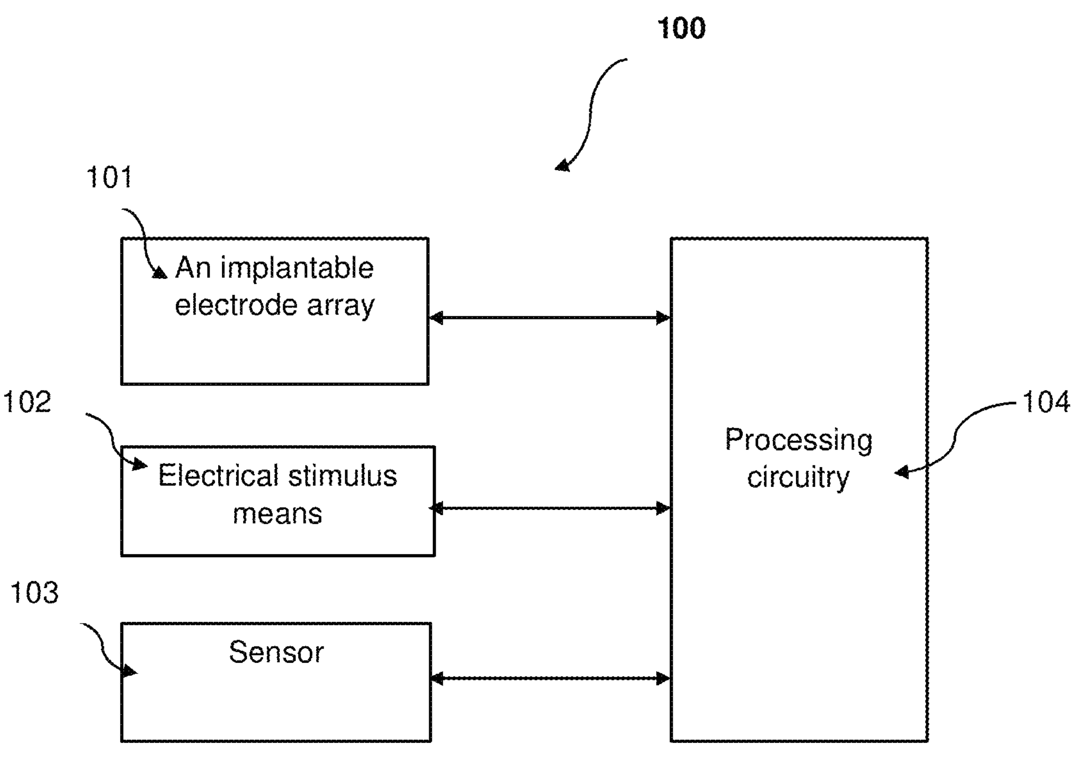
FIG. 1 illustrates a block diagram of an implantable electrical stimulation (IES) system, in accordance with an embodiment of the present application.

The present disclosure relates to an implantable electrical stimulation (IES) system. Now referring to FIG. 1, a block diagram of the implantable electrical stimulation (IES) system 100 is illustrated. The implantable electrical stimulation (IES) system 100 may include an implantable electrode array 101, an electrical stimulus means 102, a sensor 103, and a processing circuitry 104. The implantable electrical stimulation (IES) system may include, but not limited to, cochlear implant stimulation, spinal cord stimulation, retinal prosthesis, vagal nerve stimulation, deep brain stimulation, kidney implant stimulation, gastric electrical stimulation for gastroparesis, intestinal electrical stimulation, electrical stimulation for urinary incontinence, intravaginal electrical stimulation, electrical muscular stimulation, transcranial electrical stimulation, occipital nerve stimulation, brain cortical stimulation devices and other electrical stimulation devices.

In one embodiment, the processing circuitry 104 may be implemented on the server. Although the present subject matter is explained considering that the processing circuitry 104 is implemented on the server, it may be understood that the processing circuitry 104 may also be implemented in a variety of computing systems, such as a laptop computer, a desktop computer, a notebook, a workstation, a mainframe computer, a server, a network server, and the like. It will be understood that the processing circuitry 104 may be communicatively coupled to the implantable electrode array 101, the electrical stimulus means 102, the sensor 103 through a network (Not shown in the FIG. 1).

In one embodiment, the network may be a wireless network, a wired network or a combination thereof. The network can be implemented as one of the different types of networks, such as intranet, local area network (LAN), wide area network (WAN), the internet, and the like. The network may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network may include a variety of network devices, including routers, bridges, servers, computing devices, storage devices, and the like.

The processing circuitry 104 may include at least one processor. The at least one processor may be implemented as one or more microprocessors, microcomputers, microcontrollers, digital signal processors, central processing units, state machines, logic circuitries, and/or any devices that manipulate signals based on operational instructions. Among other capabilities, the at least one processor is configured to fetch and execute computer-readable instructions stored in a memory (Not shown in FIG. 1).

The memory may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes.

In another embodiment, the present disclosure also relates to an apparatus enabling an implantable electrical stimulation (IES). In this embodiment, the apparatus may be an implementation of the aforementioned implantable electrical stimulation system 100 in Field Programmable Gate Arrays (FPGA) or FPGA-like programmable devices or any other similar advanced processing devices that are prevalent in the existing art.

In one embodiment, the implantable electrode array 101 may include a plurality of electrode contacts. The electrical stimulus means 102 may be configured for applying the electrical stimulus to at least one stimulating electrode contact (Not shown in FIG. 1) of the implantable electrode array 101. The sensor 103 may be configured for sensing and determining a measured evoked compound action potential (ECAP) of the at least one stimulating electrode contact of the implantable electrode contacts to generate data for determining a plurality of parameters for the at least one stimulating electrode contact of the implantable electrode array. In one embodiment, the sensor 103 may be configured for sensing and determining the measured ECAP of the at least one stimulating electrode contact during a prescribed time period of 0.05-2 milliseconds after the application of the electrical stimulus and lasts for approximately 0.3-10 milliseconds thereafter. In one embodiment, the data generated may be used for examining the effect of the upper limit of stimulation waveforms and/or stimulation pulse widths. In another embodiment, the data generated may be used for determining optimum stimulation waveforms. In yet another embodiment, the data generated may be used for determining upper limit summation effects when stimulating multiple electrodes simultaneously or in close proximity. In yet another embodiment, the data generated may be used for measuring summation effects on bilateral or multiple implants. In still another embodiment, the data generated may be used for providing feedback for signal attenuation during use of the IES system.

The processing circuitry 104 may be configured for processing the measured ECAP and the plurality of parameters of the at least one stimulating electrode contact of the implantable electrode array 101 to compute the corresponding parameters for the remaining electrode contacts of the implantable electrode array 101.

In one embodiment, the plurality of parameters may comprise the maximum electrical current level, most comfortable stimulation current (M) level, comfortable stimulation current (C) level and threshold (T) stimulation current level.

In one embodiment, the processing circuitry 104 may be configured for creating an IES model based on a numerical method selected from a group consisting of a finite element model, a boundary element model, or any other numerical model which are well known in the art to calculate the spread of electrical current.

In another embodiment, the processing circuitry 104 may be configured for creating an IES model and adjusting the electrode position until the root mean square (RMS) error is a minimal fixed error or less than 5 μV based on the said at least one numerical method selected from a group consisting of a finite element model, a boundary element model, or any other numerical model which are well known in the art to calculate the spread of electrical current.

In yet another embodiment, the IES model may be created based on a first analytical formula to calculate the spread of electrical current. It must be noted herein that the electric current spread may be created when the electric current is injected from the at least one stimulating electrode contact.

In one embodiment, the accuracy of the spread of the electrical current may be improved by incorporating an electrode-tissue interface impedance values computed by using an electric field imaging (EFI).

In another embodiment, the spread of the electrical current may be improved by using a current steering technique in the electrical stimulation which allows the activation of neurons of the at least one stimulating electrode contact. In one exemplary embodiment, the current steering technique in the electrical stimulation may allow the activation of neurons between a pair of electrode contacts.

In one embodiment, the processing circuitry 104 may be configured for providing the spread of electric current to more than one neuron model to calculate a simulated evoked compound action potential (ECAP). In another embodiment, the processing circuitry 104 may be configured for providing the spread of electric current to a second analytical formula to calculate the simulated evoked compound action potential (ECAP).

In one embodiment, the processing circuitry 104 may be configured to calculate calibration factors (CF) of each electrode to minimize the root mean square of the fit error of the simulated ECAP with the measured ECAP using N levels of the electrical current.

In one embodiment, the processing circuitry 104 may be configured to estimate activated equivalent number of neurons at the most comfortable stimulation current (M) level, the comfortable stimulation current (C) level and the threshold (T) stimulation current level of the at least one stimulating electrode contact of the implantable electrode array based on the calibration factors (CF).

Figure 2:
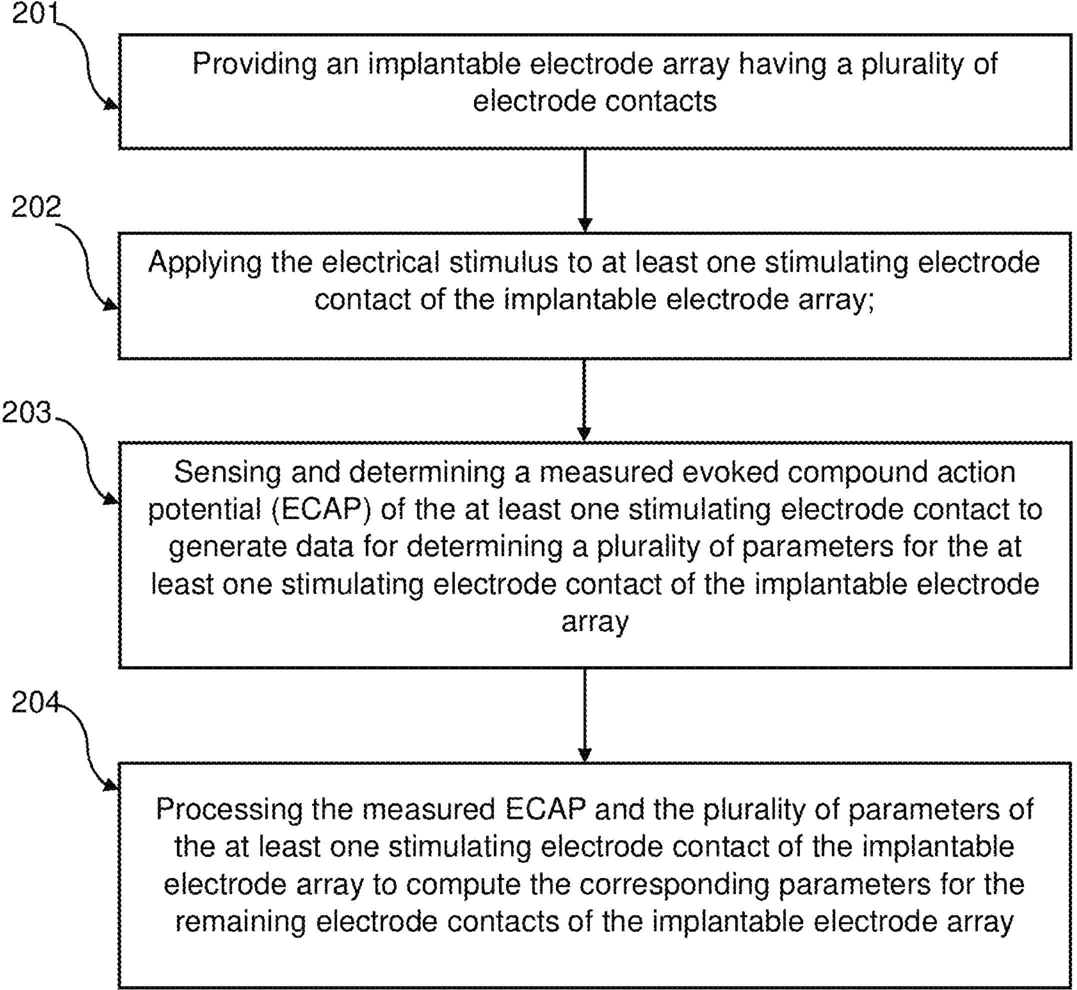
FIG. 2 illustrates a stepwise flowchart of a method for an implantable electrical stimulation, in accordance with the embodiment of the present application.

Now referring to FIG. 2, a method for an implantable electrical stimulation is illustrated. At step 201, the implantable electrode array 101 having the plurality of electrode contacts may be provided.

At step 202, the electrical stimulus means 102 may be configured for applying the electrical stimulus to the at least one stimulating electrode contact of the implantable electrode array.

At step 203, the sensor 103 may be configured for sensing and determining a measured evoked compound action potential (ECAP) of the at least one stimulating electrode contact to generate data for determining the plurality of parameters for the at least one stimulating electrode contact the implantable electrode array.

At step 204, the processing circuitry 104 may be configured for processing the measured ECAP and the plurality of parameters of the at least one stimulating electrode contact of the implantable electrode array to compute the corresponding parameters for the remaining electrode contacts of the implantable electrode array. The detailed steps performed by the processing circuitry 104 via different methods of implementation are hereinafter explained in detail as below.

For purposes of the following detailed description, different methods of implementation for cochlear implant (CI) stimulation are disclosed, however, these methods may be used for other implant stimulations such as, but not limited to, spinal cord stimulation, retinal prosthesis stimulation, vagal nerve stimulation, deep brain stimulation, kidney implant stimulation, gastric electrical stimulation for gastroparesis, intestinal electrical stimulation, electrical stimulation for urinary incontinence, intravaginal electrical stimulation, electrical muscular stimulation, transcranial electrical stimulation, occipital nerve stimulation, brain cortical stimulation and other electrical stimulations.

Figure 3:
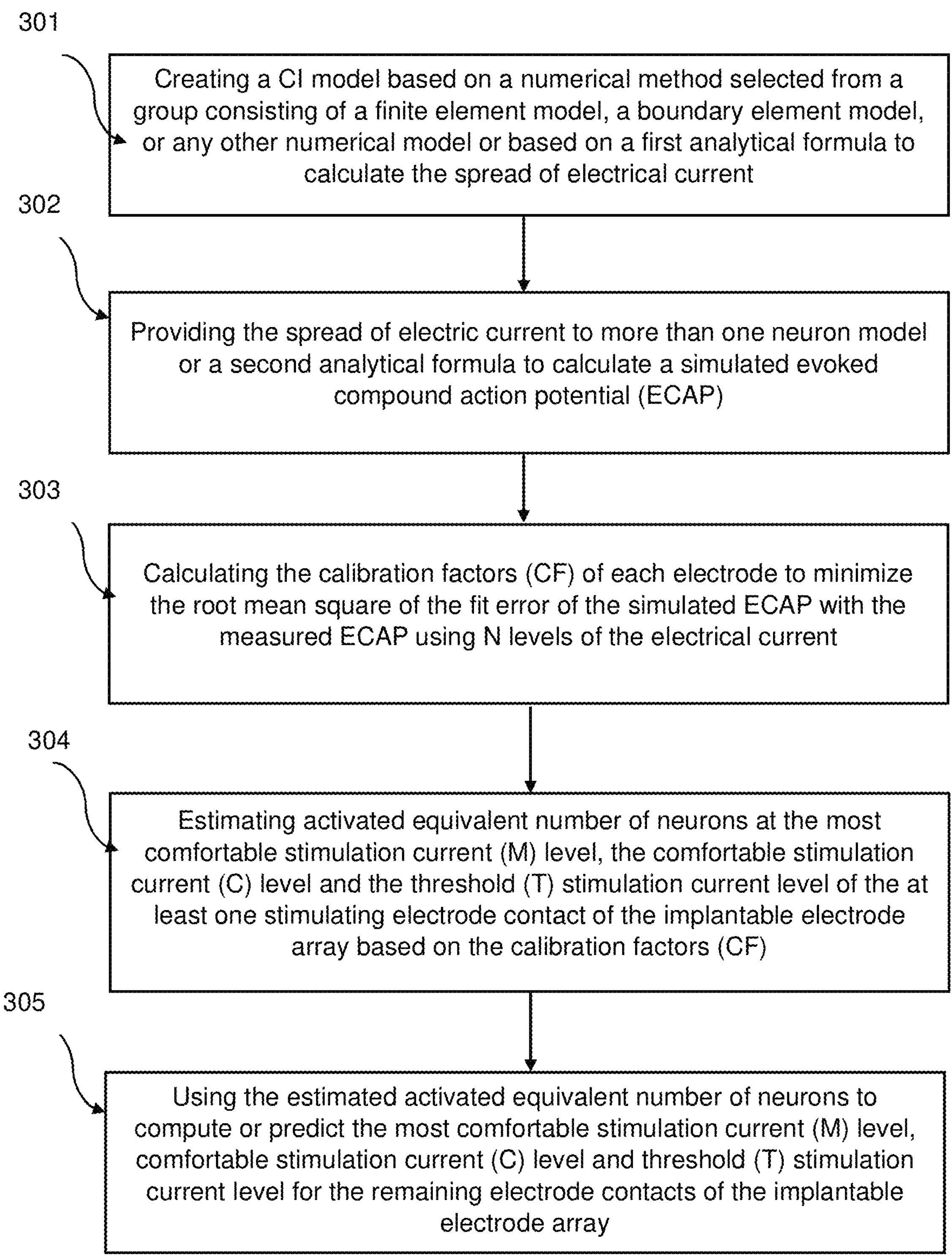
FIG. 3 illustrates a stepwise flowchart of a first method for the implantable electrical stimulation of cochlear implant (CI), in accordance with a first embodiment of the present application.

In a first embodiment, a first method for the implantable electrical stimulation of a cochlear implant (CI) is implemented when the cochlear implant (CI) electrode array trajectory is available through computed tomography (CT) or X-ray after the CI user's surgery. Now referring to FIG. 3, a stepwise flowchart of the first method for the implantable electrical stimulation of a cochlear implant (CI) is depicted, in accordance with the first embodiment of the present application.

At step 301, the processing circuitry 104 may be configured for creating a CI model based on a numerical method selected from a group consisting of a finite element model, a boundary element model, or any other numerical model which are well known in the art to calculate the spread of electrical current. In another embodiment, the processing circuitry 104 may be configured for creating a CI model based on a first analytical formula. An example of the first analytical formula is the Poisson's equation.

$$\nabla\cdot(\sigma\cdot\nabla\varphi)=0$$

where σ represents the electrical conductivity and φ stands for the electric potential. This formula is listed in a paper (Charles T. M. Choi and D. L. Wu, IEEE Transactions on Magnetics, Volume 58, No. 9, #7501404, September 2022, https://ieeexplore.ieee.org/stamp/stamp.jsp?arnumber=9776639).

Figure 4A:
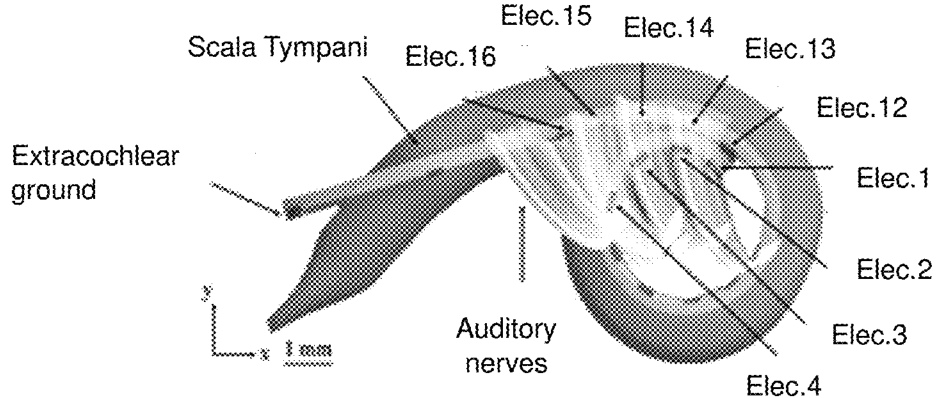
FIG. 4*a* illustrates a finite element model and a neuron model of the cochlear implant, in accordance with the first embodiment of the present application.
Figure 4B:
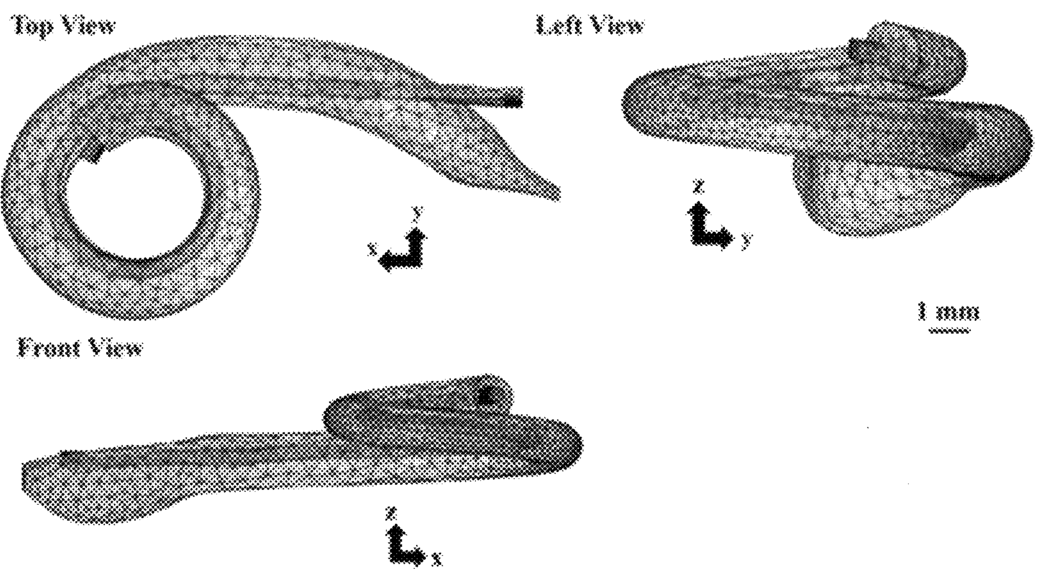
FIG. 4*b* illustrates a three-dimensional (3D) view including a top view, a left view, a front view of a mesh diagram of the finite element model of the cochlear implant, in accordance with the first embodiment of the present application.

In one embodiment, the trajectory of the implantable electrode array may be adjusted based on CT or X-ray information obtained from the CI patient after the CI surgery for creating the CI model. Now referring to FIG. 4*a*, the finite element model and a neuron model of cochlear implant (CI), in accordance with the first embodiment are illustrated. As shown in FIG. 4*a*, the cochlear implant model may be placed on scala tympani, wherein auditory nerves are also incorporated into the CI model. FIG. 4*b* illustrates three-dimensional (3D) views including a top view, a left view, and a front view of a mesh diagram of the finite element model of the cochlear implant are illustrated, in accordance with the first embodiment of the present application.

Now referring back to FIG. 3, at step 302, the processing circuitry 104 may be configured for providing the spread of electrical current to more than one neuron model to calculate a simulated evoked compound action potential (ECAP). In another embodiment, the processing circuitry 104 may be configured to provide the spread of electrical current to a second analytical formula.

An example of a second analytical formula is ECAP=A* (1−exp (−(MPI−$T_o$)/τ), where the fitted parameters are: A is the saturation level at 978.8V, MPI is the masker-probe interval and is 300 μs, $T_o$ is 430.6 s and τ is 380.5 μs. This formula is one example from FIG. 3.4 from the following source:

Onur Babacan, "Implementation of a neurophysiology-based coding strategy for the cochlear implant, January 2010" Master of Science thesis, posted at the Zurich Open Repository and Archive, University of Zurich, https://doi.org/10.5167/uzh-46000

In one embodiment, an alternating polarity technique may be used to calculate the simulated ECAP. In another embodiment, a forward masking subtraction method or other methods may be used to calculate the simulated ECAP.

Figure 5A:
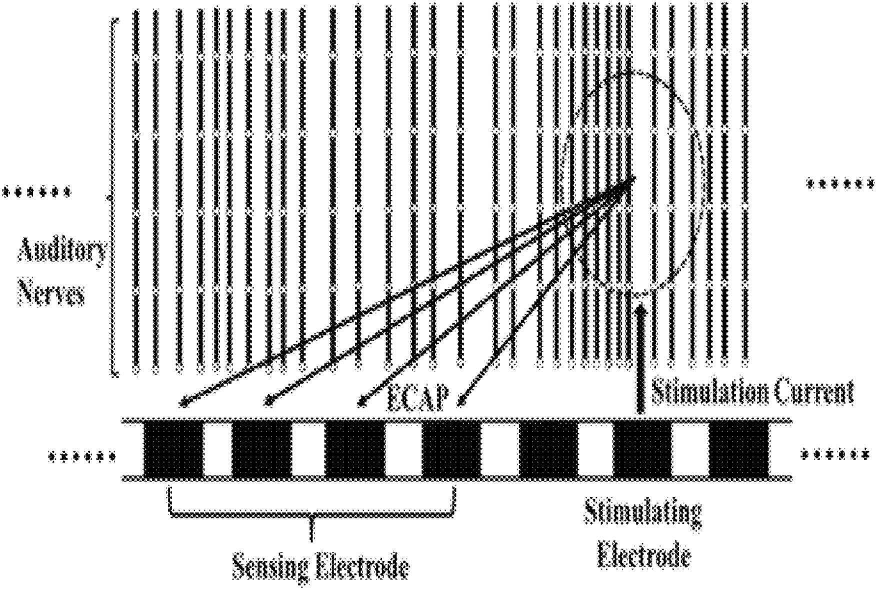
FIG. 5*a* illustrates a process of generating and recording evoked compound action potential (ECAP), in accordance with the first embodiment of the present application.
Figure 5B:
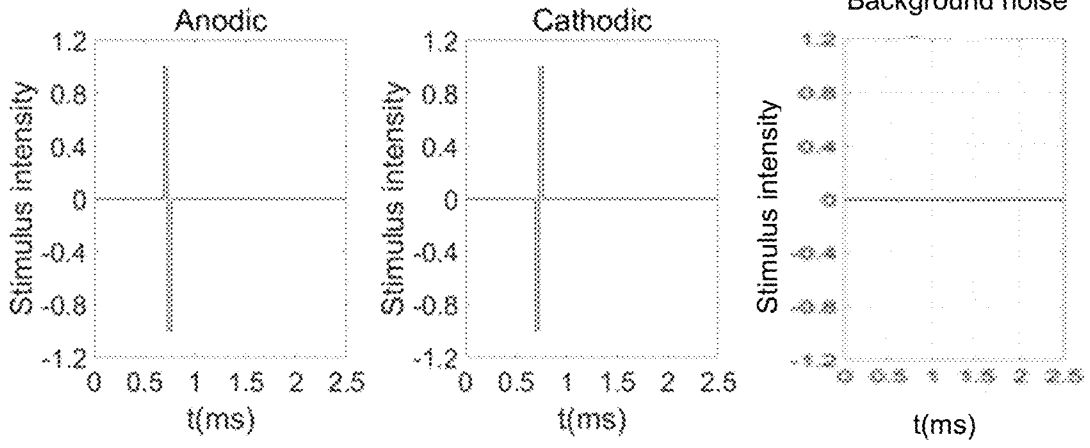
FIG. 5*b* illustrates a graphical representation of anodic ECAP response, cathodic ECAP response and background noise obtained using an alternate polarity technique, in accordance with the first embodiment of the present application.

Now referring to FIG. 5*a* process of generating and recording Evoked compound action potential (ECAP) is illustrated. As shown in FIG. 5*a*, a stimulating electrode is used to evoke ECAP. In one embodiment, a sensing electrode may be used to determine ECAP (i.e., the measured ECAP), wherein anodic and cathodic stimulating currents may be injected into the stimulating electrode. The sensing electrode may be used to measure anodic ECAP and cathodic ECAP response. Further, a zero input is applied to the stimulating electrode to measure the background noise. Now referring to FIG. 5*b*, a graphical representation of anodic ECAP response, cathodic ECAP response and background noise using the alternating polarity technique is illustrated.

The ECAP signal (i.e., the stimulated ECAP) is measured using the following equation (1):

$$\text{ECAP signal}=(\text{anodic response}+\text{cathodic response})/2-(\text{zero input response})/2 \quad \text{Eq. (1)}$$

Figure 5C:
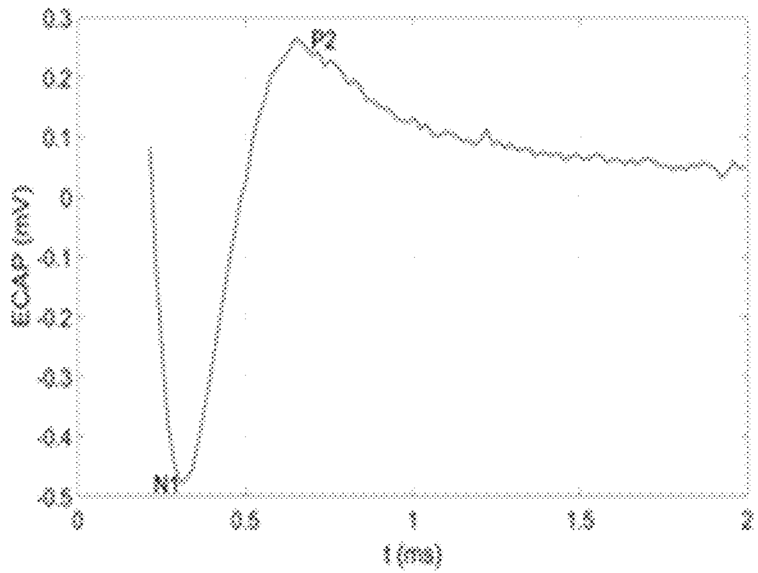
FIG. 5*c* illustrates a graphical representation of an ECAP signal in a time domain, in accordance with the first embodiment of the present application.

Now referring to FIG. 5*c*, a graphical representation of the ECAP signal in a time domain is illustrated. The ECAP signal is equal to the absolute difference between the N1 and P2 on the y-axis.

Figure 6:
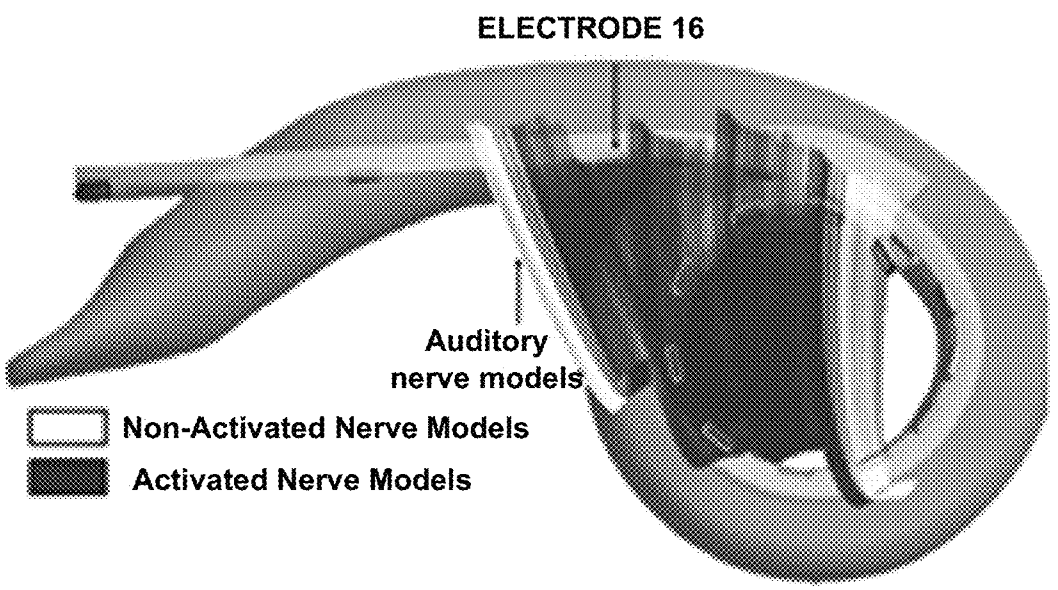
FIG. 6 illustrates an activated and non-activated neurons using the stimulation electrode at M levels of the electric current, in accordance with the first embodiment of the present application.

Now referring to FIG. 6, activated and non-activated neurons, using the stimulating electrode 16 at M levels of the electric current, are illustrated. The activated neurons at the M-level are represented in dark color in accordance with the legend.

Again, referring back to FIG. 3, at step 303, the processing circuitry 104 may be configured for calculating the calibration factor (CF) of each electrode to minimize the root mean square of the fit error of the simulated ECAP with the measured ECAP using N levels of the electrical current. In one embodiment, the measured evoked compound action potential (ECAP) may be determined before or during the CI mapping sessions. The measured ECAP may be obtained through online ECAP measurements using WIFI or Bluetooth or through the internet. In one exemplary embodiment, the measured ECAP may be determined for all four or more electrodes to be mapped or programmed during the mapping session. For each electrode, up to 2 to 4 current levels are used to determine the measured ECAP. The calibration factor for each electrode is obtained by using the following equation (2):

$$\text{Fit error}_{RMS} = \sqrt{\frac{1}{N}\sum_{i=1}^{N}(ECAP_{meas} - \text{calibration factor} \times ECAP_{sim})^2} \quad \text{Eq. (2)}$$

Now again referring back to FIG. 3, at step 304, the processing circuitry 104 may be configured for estimating the activated equivalent number of neurons at the most comfortable stimulation current (M) level, the comfortable stimulation current (C) level and the threshold (T) stimulation current level of the at least one stimulating electrode contact of the implantable electrode array based on the calibration factor (CF). The processing circuitry 104 may use the following equation (3) to estimate the "real" number of neurons activated in that particular electrode based on the number of neurons activated at the M/C/T levels in the CI model.

$$\text{Number of neuron activated}_{real} = (\text{calibration factor})\_\text{electrode} \times (\text{Number of neuron activated})\_\text{model} \quad \text{Eq. (3)}$$

In one exemplary embodiment, once the calibration factor for 1-2 electrodes of 16 or 22 electrodes are determined, the number of activated neurons may be estimated.

At step 305, the processing circuitry 104 may be configured to compute or predict the most comfortable stimulation current (M) level, comfortable stimulation current (C) level and threshold (T) stimulation current level for the remaining electrode contacts of the implantable electrode array using the estimated activated equivalent number of neurons. The said first method may predict the M (or C) levels or T levels of all other electrode contacts without actually measuring the M (or C) levels or T levels of all other electrode contacts using the traditional standard method, i.e., the behavior method. This reduces the CI mapping session time from a typical 2 hours to 1 hour or 30 minutes, depending on how many electrode contacts are measured using the behavior method. If 2 electrode contacts are measured using the traditional behavior method, then the mapping time may be reduced to 1 hour. If 1 electrode contact is measured, then the mapping time may be reduced to 30 minutes.

Figure 7:
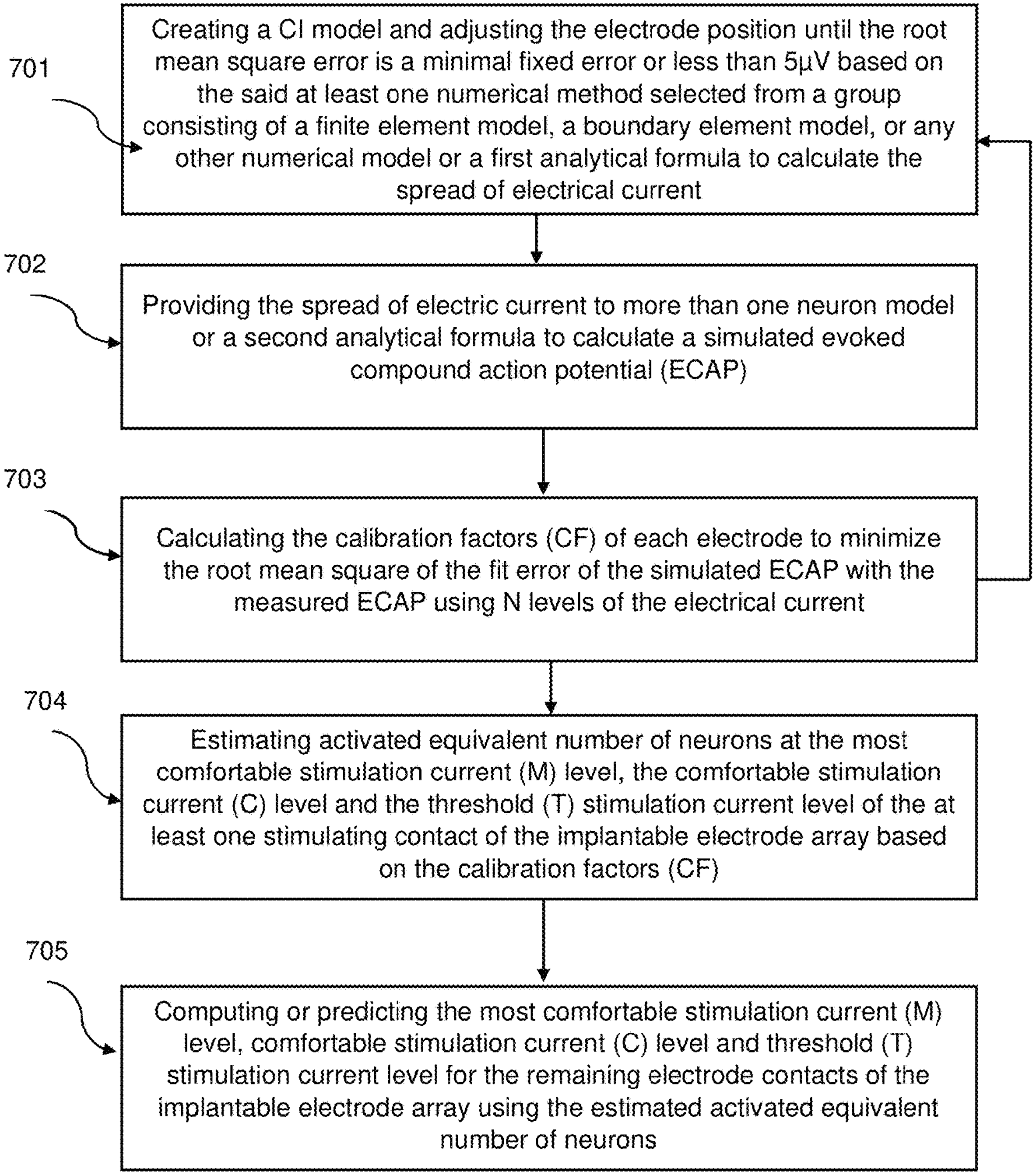
FIG. 7 illustrates a stepwise flowchart of a second method for the implantable electrical stimulation of the cochlear implant (CI), in accordance with a second embodiment of the present application.

In a second embodiment, a second method for the implantable electrical stimulation of cochlear implant (CI) is implemented when the cochlear implant (CI) electrode array trajectory is not available. FIG. 7 depicts a stepwise flowchart of the second method for the implantable electrical stimulation of cochlear implants (CI), in accordance with the second embodiment of the present application.

At step 701, the processing circuitry 104 may be configured for creating a CI model and adjusting the electrode position until the root mean square (RMS) error is a minimal fixed error or less than 5 μV based on the said at least one numerical method selected from a group consisting of a finite element model, a boundary element model, or any other numerical model which are well known in the art to calculate the spread of electrical current. The electrode position may be adjusted radially toward or away from the modiolus. It must be noted herein that the modiolus is the center of the cochlea where the auditory neurons are located. In another embodiment, the processing circuitry 104 may be configured for creating a CI model based on the first analytical formula.

At step 702, the processing circuitry 104 may be configured for providing the spread of electrical current to more than one neuron model to calculate the simulated evoked compound action potential (ECAP) using the alternating polarity technique or the forward masking subtraction method. In another embodiment, the processing circuitry 104 may be configured for providing the spread of electrical current to the second analytical formula to calculate the simulated evoked compound action potential (ECAP).

At step 703, the processing circuitry 104 may be configured for calculating the calibration factor (CF) of each electrode to minimize the root mean square of the fit error of the simulated ECAP with the measured ECAP using N levels of the electrical current. In one embodiment, the measured evoked compound action potential (ECAP) may be determined before or during the CI mapping sessions. The measured ECAP may be obtained through online ECAP measurements using WIFI or Bluetooth or through the internet. In one exemplary embodiment, the measured ECAP may be determined for all four or more electrodes to be mapped or programmed during the mapping session. For each electrode, up to 2 to 4 current levels are used to determine the measured ECAP. The calibration factor for each electrode is obtained by using equation (2). The second method goes back to step 701, after calculation of the calibration factor, wherein the electrode position may be adjusted until the root mean square (RMS) error is a minimal fixed error or less than 5p V.

Figure 8A:
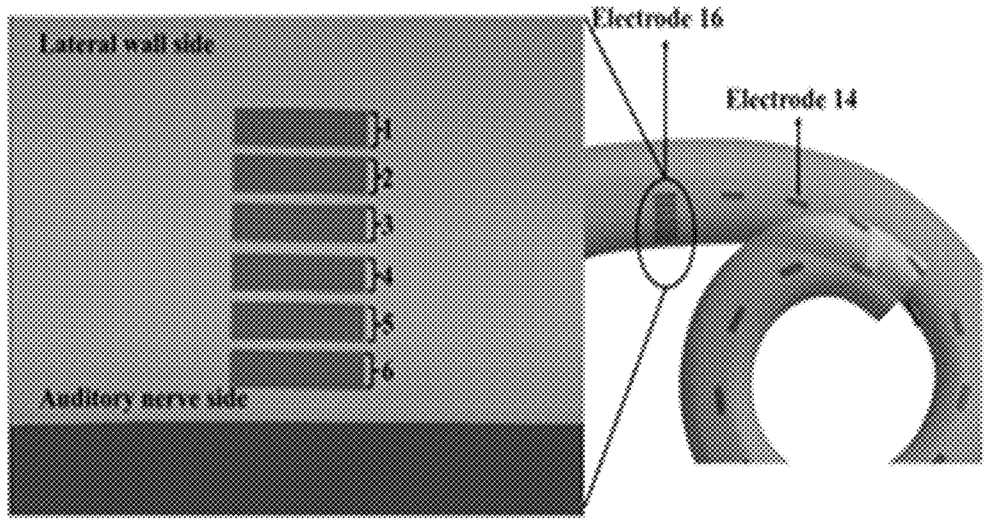
FIG. 8*a*-8*b* illustrates distinct positions of electrodes of the cochlear implant (CI) and specific positions of different electrode locations within the scala tympani, respectively, in accordance with the second embodiment of the present application.
Figure 8B:
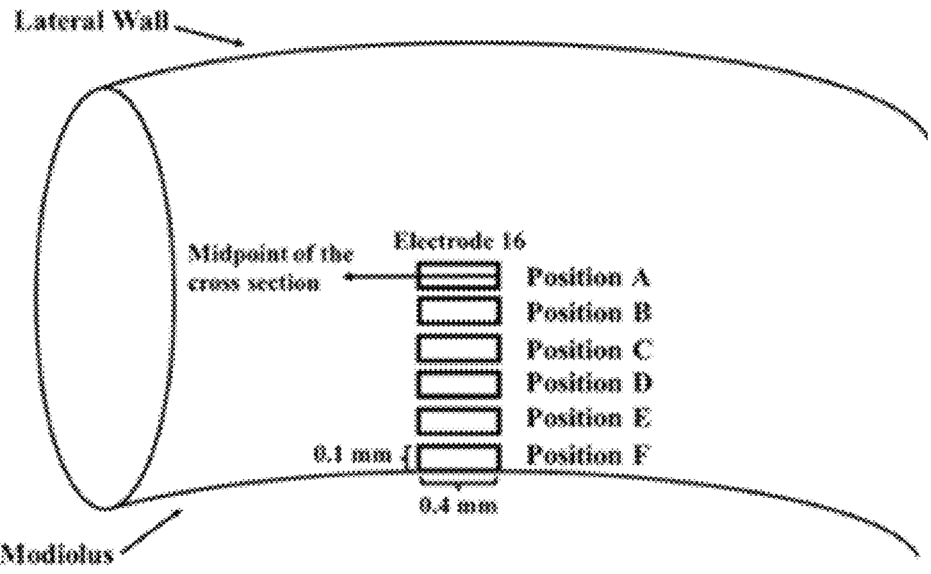

Now referring to FIG. 8*a* distinct positions of electrodes of the cochlear implant (CI) and referring to FIG. 8*b* specific positions of different electrode locations within the scala tympani, are illustrated, in accordance with the second embodiment of the present application. The lateral wall is away from the electrode, which is positioned near the auditory neurons. If the electrode is moved toward the auditory neurons, the simulated ECAP may increase. When the electrode is moved away from the auditory neurons, the simulated ECAP may decrease.

Again, referring back to FIG. 7, at step 704, the processing circuitry 104 may be configured for estimating the activated equivalent number of neurons at the most comfortable stimulation current (M) level, the comfortable stimulation current (C) level and the threshold (T) stimulation current level of the at least one stimulating electrode contact of the implantable electrode array based on the calibration factors (CF) using equation (3).

At step 705, the processing circuitry 104 may be configured to compute or predict the most comfortable stimulation current (M) level, comfortable stimulation current (C) level and threshold (T) stimulation current level for the remaining electrode contacts of the implantable electrode array using the estimated activated equivalent number of neurons. The said second method may predict the M (or C) levels or T levels of all other electrode contacts without actually measuring the M (or C) levels or T levels of all other electrode contacts using the traditional standard method, i.e., the behavior method. This may reduce the CI mapping session time from a typical 2 hours to 1 hour or 30 minutes, depending on how many electrode contacts are measured using the behavior method.

Figure 9:
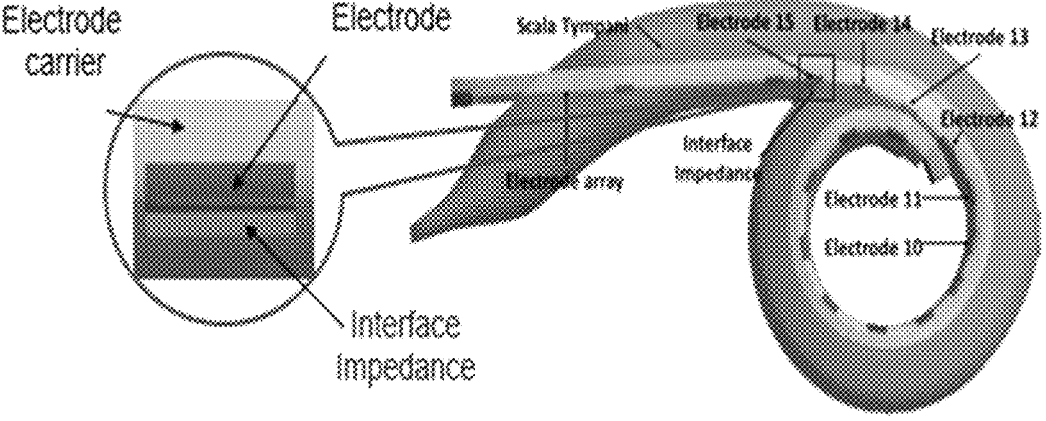
FIG. 9 illustrates a three-dimensional (3D) model with an electrode-tissue interface (EFI) signal of a third method, in accordance with a third embodiment of the present application.

In a third embodiment, the accuracy of the spread of the electrical current obtained from step 301 of the first method or step 701 of the second method may be further improved by using a third method for the implantable electrical stimulation of cochlear implant (CI). The accuracy of the spread of the electrical current may be further improved by incorporating an electrode-tissue interface impedance value using an electric field imaging (EFI) signal. Now referring to FIG. 9, a three-dimensional (3D) model with an electrode-tissue interface of the third method is illustrated. The 3D model is listed in a paper "Computing Cochlear Implant Electrode Interface Impedance based on Electric Field Imaging" published by Charles T. M. Choi, Dong Lin Wu, in 2022 IEEE 20th Biennial Conference on Electromagnetic Field Computation (CEFC), DOI: 10.1109/CEFC55061.2022, 24-26 Oct. 2022, incorporated herein by a reference. The EFI signal may be measured by injecting an electrical current into a stimulating electrode 15 (shown in FIG. 9). The EFI signal may be measured in electrodes 10-14 (shown in FIG. 9) and electrode 16 (not shown). The EFI signal may be simulated by incorporating the electrode-tissue interface impendence into the stimulating electrode 15 in the CI model.

The electrode-tissue-interface impedance value may be identified by adjusting the electrical conductivity within the electrode-tissue-interface through minimizing the fit error between EFI measurements and EFI simulation in the following equation (4) for a given electrical current input:

$$Fit\ \text{error}=(⟦ EFI⟧\_\text{meas}-⟦ EF⟧\_sim) \quad \text{Eq. (4)}$$

Once the final electrode-tissue interface is determined using equation (4), the accuracy of the spread of the electrical current obtained from step 301 of the first method or step 701 of the second method may be improved.

In a fourth embodiment, the spread of the electrical current obtained from step 301 of the first method or step 701 of the second method may be further improved by using the current steering technique in stimulating the ECAP of a fourth method for the implantable electrical stimulation of cochlear implant (CI). The current steering technique in the electrical stimulation may allow the activation of auditory neurons between electrodes instead of centered at any single electrode. Now referring to FIG. 10, activation and recording of the current steering technique for stimulating the ECAP in the fourth method is illustrated. The electric current spread is created when current is injected from stimulating electrodes 2 and 3. The auditory nerves within such a field may be excited to generate action potentials, which is recorded by the recording electrodes close to the stimulating electrodes. The ratio of the currents injected in electrodes 2 and 3 is determined by the parameter a of equation (5):

$$I_{Stim2}=I_{Total}\times\alpha$$

$$I_{Stim3}=I_{Total}\times(1-\alpha) \quad \text{Eq (5)}$$

with $0\le\alpha\le1$

Figure 10:
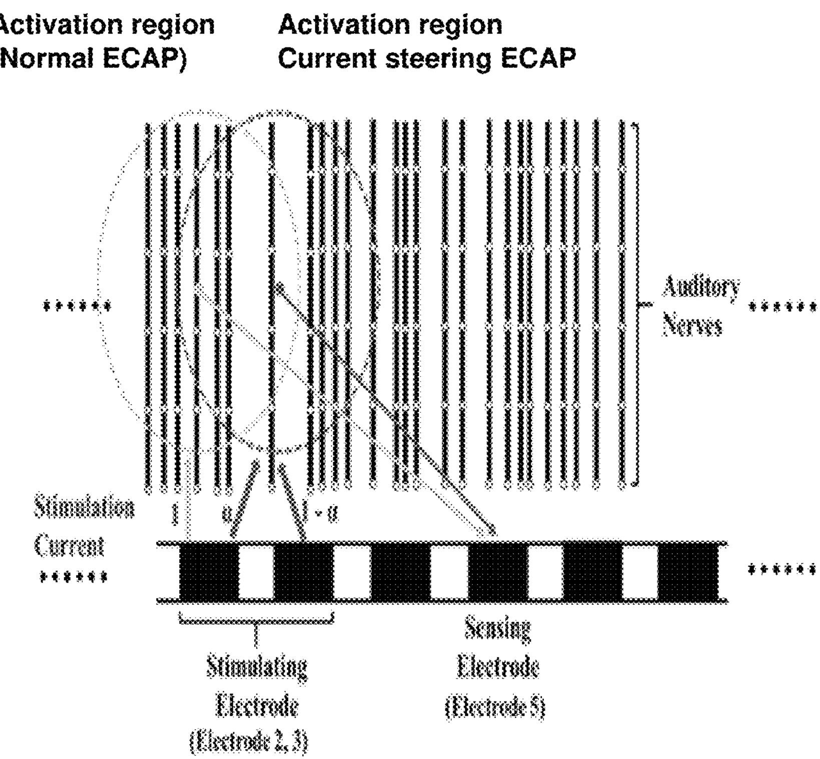
FIG. 10 illustrates an activation and recording of a current steering technique for stimulated ECAP in a fourth method, in accordance with a fourth embodiment of the present application.

I_stim2 and I_stim3 represent the current injected into Electrodes 2 and 3 as illustrated in FIG. 10, respectively. The first and second methods for the implantable stimulation (IES) of cochlear implant (CI) may be limited to only a fixed number of stimulation sites i.e., only 16 stimulation sites for a 16-electrode system. The current steering technique of the fourth method may allow continuous scanning of the auditory neurons along the cochlea with an infinite number of electrical stimulation sites by adjusting the a.

Figure 12:
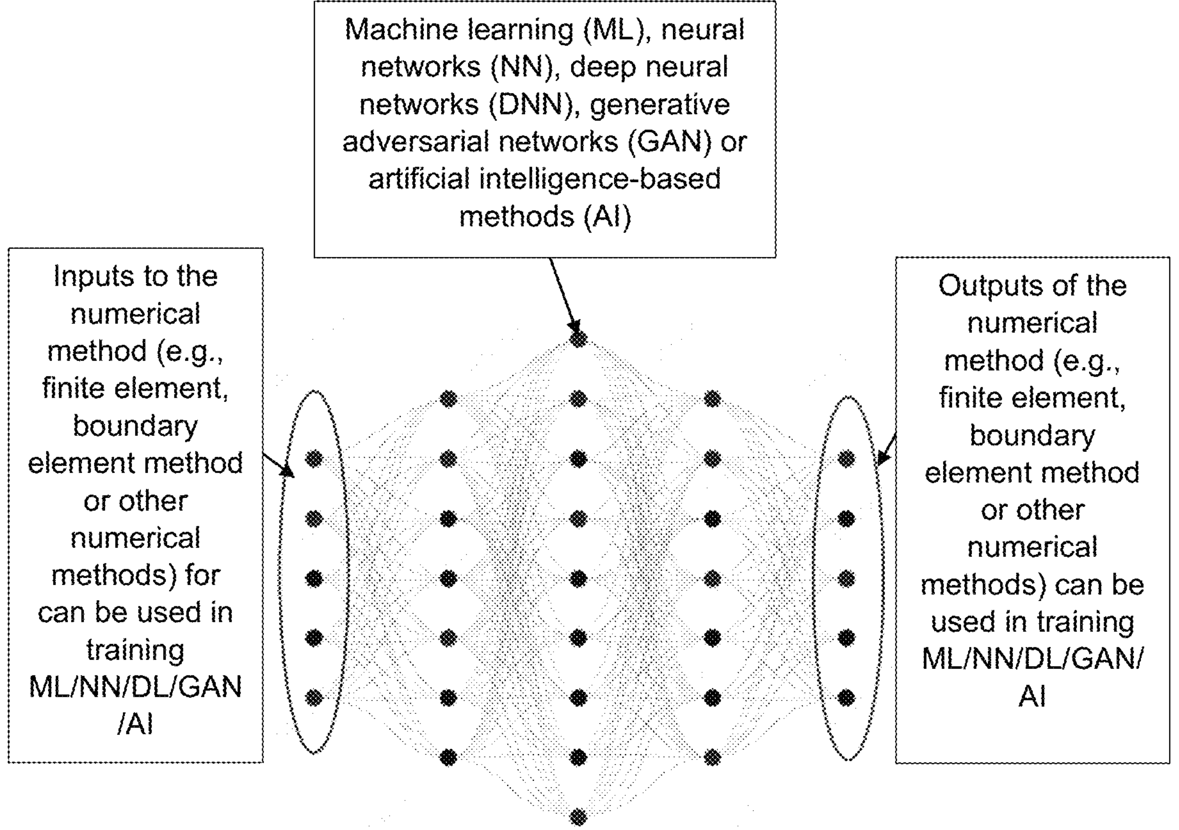
FIG. 12 and FIG. 13 illustrate the methods implemented by artificial intelligence (AI) based techniques, in accordance with the fifth embodiment of the present application

In a fifth embodiment of the present application, a fifth method of an artificial intelligence-based method for the implantable electrical stimulation of cochlear implant (CI) is implemented. Now referring to FIG. 11, the fifth method of the artificial intelligence (AI) based method for the implantable stimulation implant (IES), is illustrated. At step 1101, the processing circuitry 104 may be configured for training a first machine learning (ML)model, a first neural network (NN), a first generative adversarial network (GAN), a first deep neural network (DNN) model or other first Artificial Intelligence (AI) based methods for computing the electric current spread using the said numerical method selected from a group consisting of a finite element model, a boundary element model, or any other numerical model which are well known in the art. FIG. 12 depicts an exemplary embodiment of the step 1101. The inputs to the numerical method may be used as training the input of the first machine learning (ML) model, the first neural network (NN) model, the first Deep neural network (DNN) model, the first generative adversarial network (GAN) model or the first Artificial Intelligence (AI) based method. Further, an output of the numerical method may be used for training the output of the first machine learning (ML) model, the first neural network (NN) model, the first Deep neural network (DNN) model, the first generative adversarial network (GAN) model or the first Artificial intelligence (AI) based method. After training, the output of the numerical method may be the spread of the electrical current. When the first machine learning (ML) model, the first neural network (NN) model, the first Deep neural network (DNN) model, the first generative adversarial network (GAN) model or the first Artificial Intelligence (AI) based method is trained, then the first machine learning (ML) model, the first neural network (NN) model, the first Deep neural network (DNN) model, the first generative adversarial network (GAN) model or the first Artificial Intelligence (AI) based method may be used to replace the numerical-based methods to calculate the spread of the electrical current.

Figure 13:
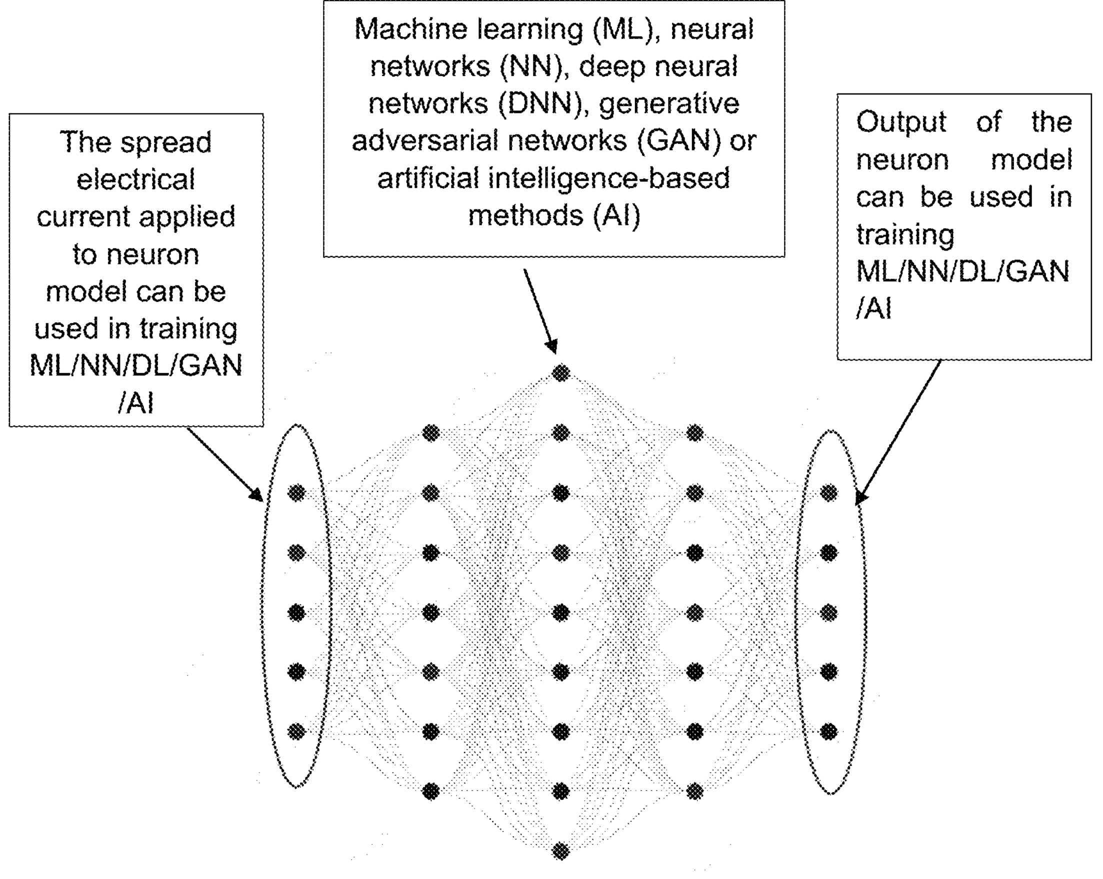

Again referring back to FIG. 11, at step 1102, the processing circuitry 104 may be configured for providing an output of the first machine learning (ML) model, the first neural network (NN), the first generative adversarial network (GAN), the first deep neural network (DNN) model or other first artificial intelligence (AI) based methods to a second machine learning (ML) model, a second neural network (NN), a second generative adversarial network (GAN), a second deep neural network (DNN) model or a second artificial intelligence (AI) based method to calculate the number of neurons being activated to compute or predict the most comfortable stimulation current (M) level, comfortable stimulation current (C) level and threshold (T) stimulation current level for the remaining electrode contacts of the implantable electrode array. FIG. 13 depicts an exemplary embodiment of the step 1102. The spread of the electrical current applied to the neuron model may be used for training the input of the second machine learning (ML) model, the second neural network (NN) model, the second Deep neural network (DNN) model, the second generative adversarial network (GAN) model or the second Artificial intelligence (AI) based method. Further, an output of the neuron model may be used for training the output of the second machine learning (ML) model, the second neural network (NN) model, the second Deep neural network (DNN) model, the second generative adversarial network (GAN) model or the second Artificial intelligence (AI) based method. When the second machine learning (ML) model, the second neural network (NN) model, the second Deep neural network (DNN) model, the second generative adversarial network (GAN) model or the second Artificial Intelligence (AI) based method is trained, then the second machine learning (ML) model, the second neural network (NN) model, the second Deep neural network (DNN) model, the second generative adversarial network (GAN) model or the second Artificial Intelligence (AI) based method may be used to replace the neuron models to calculate the number of neurons being activated.

In one embodiment, the aforementioned method steps performed by the processing circuitry 104 may implemented using a non-transitory computer readable medium storing a program including a plurality of programmed instructions. The 'non-transitory computer-readable medium' as used herein encompasses any tangible storage medium which may store instructions which are executable by a processor of a computing device. The computer-readable medium may be referred to as a computer-readable non-transitory storage medium. The computer-readable medium may also be referred to as a tangible computer readable medium. In some embodiments, a computer-readable medium may also be able to store data which is able to be accessed by the processor of the computing device. Examples of computer-readable media include, but are not limited to: a floppy disk, a magnetic hard disk drive, a solid-state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-medium also refers to various types of recording media capable of being accessed by the computer device via a network or communication link. For example, a data may be retrieved over a modem, over the internet, or over a local area network.

The implantable electrical stimulation (IES) system and the method of the present application may enable the automatic programming of the electrical stimulation devices. The automatic programming of the electrical stimulation devices may be done remotely through the internet, Wi-Fi, Bluetooth and other communication methods.

Once the initial programming or mapping parameters are provided as an open-loop or closed-loop system, the IES system may maintain a specific electrical stimulation level even if the human bodies have changed significantly after a period of time.

The initial programming or mapping parameters may be used to calibrate the plurality of parameters of the remaining electrodes. The initial programming or mapping parameters may be based on measurement manually by clinicians or by other means.

Although implementations for the implantable electrical stimulation (IES) system, apparatus, non-transitory computer-readable medium, and the methods thereof have been described in language specific to structural features, it is to be understood that the appended claims are not necessarily limited to the specific features described. Rather, the specific features are disclosed as examples of implementations of the implantable electrical stimulation (IES) system, apparatus, non-transitory computer-readable medium, and the methods thereof.

What is claimed is:

1. An implantable electrical stimulation (IES) system, comprising:
- an implantable electrode array having a plurality of electrode contacts;
- an electrical stimulus means for applying the electrical stimulus to at least one stimulating electrode contact of the implantable electrode array;
- a sensor for sensing and determining a measured evoked compound action potential (ECAP) of the at least one stimulating electrode contact to generate data for determining a plurality of parameters for the at least one stimulating electrode contact of the implantable electrode array; and
- a processing circuitry configured for:
  - creating an implantable electrical stimulation (IES) model and adjusting an electrode position until a root mean square (RMS) error is a minimal fixed error or less than 5μ V to calculate a spread of electrical current,
  - calculating a simulated evoked compound action potential (ECAP) based on the spread of electrical current,
  - processing the measured ECAP and the simulated ECAP to calculate a calibration factor (CF) of each electrode to minimize a root mean square of the fit error between the simulated ECAP and the measured ECAP using N levels of the electrical current for calibrating stimulation parameters of the electrode array, and processing the measured ECAP, the simulated ECAP, the calibration factor (CF), and the plurality of parameters of the at least one stimulating electrode contact of the implantable electrode array to compute the corresponding parameters for the remaining electrode contacts of the implantable electrode array.

2. The implantable electrical stimulation (IES) system of claim 1, wherein the sensor is configured for sensing and determining the measured ECAP of the at least one stimulating electrode contact during a prescribed time period of 0.05-2 milliseconds after the application of the electrical stimulus and lasts for approximately 0.3-10 milliseconds thereafter.

3. The implantable electrical stimulation (IES) system of claim 1, wherein the processing circuitry is configured to perform the following processing steps:

creating the IES model and adjusting the electrode position based on a numerical method selected from a group consisting of a finite element model, a boundary element model, or any other numerical model to calculate the spread of electrical current.

4. The implantable electrical stimulation (IES) system of claim 3, wherein the accuracy of the spread of electrical current is improved by incorporating electrode-tissue interface impedance values computed by using an electric field imaging (EFI) or using a current steering technique in the electrical stimulation which allows an activation of neurons of the at least one stimulating electrode contact.

5. The implantable electrical stimulation (IES) system of claim 3, wherein the processing circuitry is configured for providing the spread of electrical current to more than one neuron model or to a second analytical formula to calculate the simulated ECAP.

6. The implantable electrical stimulation (IES) system of claim 1, wherein the plurality of parameters comprises a maximum electrical current level, a most comfortable stimulation current (M) level, a comfortable stimulation current (C) level, and a threshold (T) stimulation current level, and wherein the processing circuitry is configured to estimate the activated equivalent number of neurons at the most comfortable stimulation current (M) level, the comfortable stimulation current (C) level, and the threshold (T) stimulation current level of the at least one stimulating electrode contact of the implantable electrode array based on the calibration factors (CF).

7. The implantable electrical stimulation (IES) system of claim 6, wherein the processing circuitry is configured to use the estimated activated equivalent number of neurons to compute or predict the most comfortable stimulation current (M) level, the comfortable stimulation current (C) level, and the threshold (T) stimulation current level for the remaining electrode contacts of the implantable electrode array.

8. The implantable electrical stimulation (IES) system of claim 3, wherein the processing circuitry is configured to train a first machine learning (ML) model, a first neural network (NN), a first deep neural network (DNN) model, a first generative adversarial network (GAN) or a first Artificial Intelligence (AI) based method for computing the electrical current spread using the said numerical method.

9. The implantable electrical stimulation (IES) system of claim 8, wherein the processing circuitry is configured to provide an output of the first machine learning (ML) model, the first neural network (NN), the first deep neural network (DNN) model, the first generative adversarial network (GAN) or the first Artificial Intelligence (AI) based method to a second machine learning (ML) model, a second neural network (NN), a second deep neural network (DNN) model, a second generative adversarial network (GAN) or a second Artificial Intelligence (AI) based method to calculate the number of neurons being activated to compute or predict the most comfortable stimulation current (M) level, the comfortable stimulation current (C) level, and the threshold (T) stimulation current level for the remaining electrode contacts of the implantable electrode array.

10. A method for an implantable electrical stimulation (IES), comprising:

providing, an implantable electrode array having a plurality of electrode contacts;

applying, via an electrical stimulus means, the electrical stimulus to at least one stimulating electrode contact of the implantable electrode array;

sensing and determining, via a sensor, a measured evoked compound action potential (ECAP) of the at least one stimulating electrode contact to generate data for determining a plurality of parameters for the at least one stimulating electrode contact of the implantable electrode array; and creating, via a processing circuitry, an implantable electrical stimulation (IES) model and adjusting an electrode position until a root mean square (RMS) error is a minimal fixed error or less than 5μ V to calculate a spread of electrical current;

calculating, via the processing circuitry, a simulated evoked compound action potential (ECAP) based on the spread of electrical current;

processing, via the processing circuitry, the measured ECAP and the simulated ECAP to calculate a calibration factor (CF) of each electrode to minimize a root mean square of the fit error between the simulated ECAP and the measured ECAP using N levels of the electrical current for calibrating stimulation parameters of the electrode array; and processing, via the processing circuitry, the measured ECAP, the simulated ECAP, the calibration factor (CF), and the plurality of parameters of the at least one stimulating electrode contact of the implantable electrode array to compute the corresponding parameters for the remaining electrode contacts of the implantable electrode array.

11. The method of claim 10, wherein the sensing and determining the measured ECAP of the at least one stimulating electrode contact is performed during a prescribed time period of 0.05-2 milliseconds following the application of the electrical stimulus and lasts for approximately 0.3-10 milliseconds thereafter.

12. The method of claim 10, wherein the method comprises:

creating, via the processing circuitry, the IES model and adjusting the electrode position based on numerical methods consisting of a finite element model, a boundary element model or any other numerical model to calculate the spread of electrical current.

13. The method of claim 12, wherein the accuracy of the spread of electrical current is improved by incorporating electrode-tissue interface impedance values computed by using an electric field imaging (EFI) or using a current steering technique in the electrical stimulation which allows an activation of neurons through the at least one stimulating electrode contact.

14. The method of claim 12, wherein the method comprises a step for providing the spread of electrical current to more than one neuron model or to a second analytical formula to calculate the simulated ECAP.

15. The method of claim 10, wherein the plurality of parameters comprises a maximum electrical current level, a most comfortable stimulation current (M) level, a comfortable stimulation current (C) level, and a threshold (T) stimulation current level, and wherein the processing circuitry is configured to estimate the activated equivalent number of neurons at the most comfortable stimulation current (M) level, the comfortable stimulation current (C) level, and the threshold (T) stimulation current level of the at least one stimulating electrode contact of the implantable electrode array based on the calibration factors (CF).

16. The method of claim 15, wherein the method comprises a step for computing or predicting the most comfortable stimulation current (M) level, the comfortable stimulation current (C) level, and the threshold (T) stimulation current level for the remaining electrodes of the implantable electrode array using the estimated activated equivalent number of neurons.

17. The method of claim 12, wherein the method comprises a step for training a first machine learning (ML) model, a first neural network (NN), a first deep neural network (DNN) model, a first generative adversarial network (GAN) or a first Artificial Intelligence (AI) based method for computing the electrical current spread using the numerical methods.

18. The method of claim 17, wherein the method comprises a step for providing an output of the first machine learning (ML) model, the first neural network (NN),the generative adversarial network (GAN), the first deep neural network (DNN) model, the first generative adversarial network (GAN) or the first Artificial Intelligence (AI) based method to a second machine learning (ML) model, a second neural network (NN), a second deep neural network (DNN) model, a second generative adversarial network (GAN) or a second Artificial Intelligence (AI) based method to calculate the number of neurons being activated to compute or predict the most comfortable stimulation current (M) level, the comfortable stimulation current (C) level, and the threshold (T) stimulation current level for the remaining electrode contacts of the implantable electrode array.

19. An apparatus enabling an implantable electrical stimulation (IES), comprising:

an implantable electrode array having a plurality of electrode contacts;

an electrical stimulus means for applying the electrical stimulus to at least one stimulating electrode contact of the implantable electrode array;

a sensor for sensing and determining a measured evoked compound action potential (ECAP) of the at least one stimulating electrode contact to generate data for determining a plurality of parameters for the at least one stimulating electrode contact of the implantable electrode array; and a processing circuitry configured for:

creating an implantable electrical stimulation (IES) model and adjusting an electrode position until a root mean square (RMS) error is a minimal fixed error or less than 5μ V to calculate a spread of electrical current, calculating a simulated evoked compound action potential (ECAP) based on the spread of electrical current, processing the measured ECAP and the simulated ECAP to calculate a calibration factor (CF) of each electrode to minimize a root mean square of the fit error between the simulated ECAP and the measured ECAP using N levels of the electrical current for calibrating stimulation parameters of the electrode array, and processing the measured ECAP, the simulated ECAP, the calibration factor (CF), and the plurality of parameters of the at least one stimulating electrode contact of the implantable electrode array to compute the corresponding parameters for the remaining electrode contacts of the implantable electrode array.

20. The apparatus of claim 19, wherein the sensing and determining the measured ECAP of the at least one stimulating electrode contact is performed by the sensor during a prescribed time period of 0.05-2 milliseconds following the application of the electrical stimulus and lasts for approximately 0.3-10 milliseconds thereafter.

21. The apparatus of claim 19, wherein the processing circuitry is further configured for:

creating the IES model and adjusting the electrode position based on numerical methods consisting of a finite element model, a boundary element model or any other numerical model to calculate the spread of electrical current.

22. A non-transitory computer readable medium storing a program enabling an implantable electrical stimulation (IES), the program comprising a plurality of programmed instructions, the plurality of programmed instructions comprising instructions for:

receiving a measured evoked compound action potential (ECAP) of at least one stimulating electrode contact of an implantable electrode array from a sensor to generate data for determining a plurality of parameters for the at least one stimulating electrode contact of the implantable electrode array;

creating an implantable electrical stimulation (IES) model and adjusting an electrode position until a root mean square (RMS) error is a minimal fixed error or less than 5μ V to calculate a spread of electrical current;

calculating a simulated evoked compound action potential (ECAP) based on the spread of electrical current;

processing the measured ECAP and the simulated ECAP to calculate a calibration factor (CF) of each electrode to minimize a root mean square of the fit error between the simulated ECAP and the measured ECAP using N levels of the electrical current for calibrating stimulation parameters of the electrode array; and processing the measured ECAP, the simulated ECAP, the calibration factor (CF), and the plurality of parameters of the at least one stimulating electrode contact of the implantable electrode array to compute the corresponding parameters for the remaining electrode contacts of the implantable electrode array.

23. The non-transitory computer readable medium of claim 22, wherein the plurality of programmed instructions comprises instructions for:

creating the IES model and adjusting the electrode position based on numerical methods consisting of a finite element model, a boundary element model or any other numerical model to calculate the spread of electrical current.

* * * * *